United States Patent [19]

May et al.

[11] 4,425,186

[45] Jan. 10, 1984

[54] DIMETHYLAMIDE AND CATIONIC SURFACTANT DEBONDING COMPOSITIONS AND THE USE THEREOF IN THE PRODUCTION OF FLUFF PULP

[75] Inventors: Oscar W. May; Philip M. Hoekstra, both of Memphis, Tenn.

[73] Assignee: Buckman Laboratories, Inc., Memphis, Tenn.

[21] Appl. No.: 247,187

[22] Filed: Mar. 24, 1981

[51] Int. Cl.$^3$ .............................................. D21H 3/10
[52] U.S. Cl. ..................................... 162/158; 162/179
[58] Field of Search ................................ 162/158, 179

[56] References Cited

U.S. PATENT DOCUMENTS 3,554,862 1/1971 Hervey et al. ....................... 162/158
3,554,863 1/1971 Hervey et al. ....................... 162/158
3,677,886 7/1972 Forssblad et al. ....................... 162/5
4,198,247 4/1980 Flaherty ............................... 162/158

FOREIGN PATENT DOCUMENTS 2819039 11/1979 Fed. Rep. of Germany ...... 162/179
50-59503 5/1975 Japan ................................... 162/179

Primary Examiner—William F. Smith
Attorney, Agent, or Firm—Floyd Trimble

[57] ABSTRACT

A mixture comprising a cationic surfactant and a dimethylamide of a straight chain carbon carboxylic acid containing 12 to 18 carbon atoms is useful in the treatment of cellulose pulp to reduce inter-fiber bonding, thus obtaining a low mechanical strength pulp sheet and having little or no adverse effects upon the hydrophilic properties of said fibers.

23 Claims, No Drawings

DIMETHYLAMIDE AND CATIONIC SURFACTANT DEBONDING COMPOSITIONS AND THE USE THEREOF IN THE PRODUCTION OF FLUFF PULP

This invention relates to the treatment of cellulose pulp fiber whereby the conventional pulp sheet or board formed on a papermaking machine, which is normally very difficult to fiberize, is modified so that the resulting sheet or board is easily fiberized by mechanical means. More particularly, this invention relates to a fiber debonding process involving the impregnation of cellulose pulp fiber with a composition comprising a cationic surfactant and a dimethylamide of a carboxylic acid containing 12 to 18 carbon atoms.

Batts of cellulosic, fluffy material are commonly produced by mechanically defiberizing dried pulpboard sheets and air forming the resulting fibers. For many purposes the pulpboard is well adapted for conversion into fluff and, additionally, it is of low cost and readily handleable. The mechanical action involved in defiberizing, however, tends to cause the fluff batts to be dusty and, unless embossed or enclosed, the fluff tends to be excessively dusty, that is, to contain an undesirable quantity of fines. Furthermore, mechanical defiberizing processes entail the expenditure of a great deal of energy.

Many compositions broadly defined as cationic surfactants have been suggested for use as fiber debonding agents in an attempt to overcome the difficulties inherent in mechanical defiberizing processes. None of the methods heretofore suggested as a means of overcoming these disadvantages, however, have been entirely satisfactory. Some cause foaming, some are irritating and many have an adverse effect upon the hydrophilic properties of the final product.

One solution to the foregoing problems is found in U.S. Pat. No. 3,395,708, issued to Laurence R. B. Hervey and Donald K. George on Aug. 6, 1968, which patent discloses the use of a specific class of cationic debonding agents to result in a comminution-prone wood pulp sheet. While it is true that certain benefits in ease of comminution and in resultant air-laid product characteristics result from use of the cationic debonding agents disclosed by the aforementioned patent, the cationic debonding agents, for example dimethyldihydrogenated tallow quaternary ammonium chloride, achieve comminution ease in a wood pulp sheet at a considerable disadvantage to both absorbent rate and total absorbent capacity in subsequent air-laid products. Although a wood pulp sheet without surfactant impregnation is difficult to comminute or fiberize in the preparation of air-carried fibrous masses to be deposited on foraminous media in the air-laid process, the characteristics of both absorbent rate and absorbent capacity of an air-laid pad prepared from such materials is in fact superior to that prepared from wood pulp sheets impregnated with a cationic debonding agent.

These same patentees in U.S. Pat. No. 3,554,862 disclose a method of rendering a fibrous wood pulp sheet easily fiberizable by partially debonding the normally self-bonding fibers of the sheet by impregnating a wet slurry of wood pulp with a long chain cationic surfactant, forming the slurry into a sheet, and drying the sheet. Subsequent mechanical fiberization of this dry pulp sheet produces a soft fluff with a minimum of undesirable residual particles and a minimum of fiber damage. This fluff is air-laid to form batts with good loft, moisture absorption, and strength. The surfactants said to be useful as debonding agents are long chain cationic surfactants with at least 12 carbon atoms in at least one alkyl chain, and illustrative specific examples of same are fatty dialkyl quaternary amine salts, mono fatty alkyl tertiary amine salts, primary amine salts, and unsaturated fatty alkyl amine salts.

When a cationic surfactant is added to a pulp slurry, it is attracted to the negatively charged cellulose fibers. Adsorption of the cationic compound onto the surface leaves the hydrocarbon chains exposed and the thin hydrophobic coating prevents extensive development of fiber-to-fiber bonds. Thus mechanical fiberization of the dried pulp is facilitated. However, this hydrophobic film on the fiber surface also reduces the water absorbency of the normally highly hydrophilic cellulose. This reduction in absorptiveness is undesirable when fluff produced from the pulp is to be used in products that are supposed to be highly absorbent, such as diapers and other sanitary products. Although the wettability of the fibers in this fluff can be improved by a subsequent treatment with a wetting agent, this requires an additional, separate operation.

It is, therefore, a principal object of the present invention to provide a composition and process useful as a debonding agent for cellulose fluff fibers that obviates the disadvantages of the prior art.

It is another object of our invention to provide a composition and process useful as a debonding agent for cellulose fluff fiber that is effective over a wide range of concentrations and physical environments.

These and other objects and advantages of the processes and compositions will become apparent as the description proceeds.

To the accomplishment of the foregoing and related ends, this invention then comprises the features hereinafter fully described and particularly pointed out in the claims, the following description setting forth in detail certain illustrative embodiments of the invention, these being indicative, however, of but a few of the various ways in which the principles of the invention may be employed.

Briefly stated, we have discovered that the addition of a relatively small amount of a composition comprising an N,N-dimethylamide of a straight chain carboxylic acid and a cationic surfactant to wet cellulose pulp fibers is very effective as a fiber debonding agent and that such a composition has little or no adverse effect on the hydrophilic properties of said fibers.

Before proceeding with specific examples illustrating our invention, it may be well to indicate in general the nature of the materials required in the process.

Suitable N,N-dimethylamides of carboxylic acids are prepared from straight chain carboxylic acids containing from 12–18 carbon atoms. Although any carboxylic acid containing from 12–18 carbon atoms is suitable in our process, we prefer those containing 18 carbon atoms as such acids are readily available in large quantities at economical costs. These preferred acids are further characterized by having at least one carbon to carbon double bond. Specific acids classified within this category include: oleic, linoleic, linolenic, ricinoleic, and mixtures thereof. Also suitable are the mixed acids found in tall, castor, corn, cottonseed, linseed, olive, peanut, rapeseed, safflower, sesame, and soybean oils. A mixture of carboxylic acids particularly suitable for use in our invention is that available commercially as tall oil fatty acids under the trademark Unitol ACD Special. A typical analysis of this product is as follows:

TABLE

| | Typical analysis |
|---|---|
| Fatty acids, pct | 97.5 |
| Rosin acids, pct | 1.0 |
| Unsaponifiables, pct | 1.5 |
| Linoleic acid, pct | 45.1 |
| Oleic acid, pct | 49.5 |
| Saturated acid, pct | 1.6 |
| Acid number | 195.0 |
| Saponification number | 197.0 |
| Color, Gardner | 3.0 |
| Specific gravity, 25° C./25° C. | 0.902 |
| Titre, °C. | 2.0 |
| Flash point, °F. | 380.0 |
| Fire point, °F. | 423.0 |

The N,N-dimethylamides of these tall oil fatty acids will sometimes hereinafter be referred to as DMA.

Suitable cationic surfactants for use in our invention include those of aliphatic, carbocyclic, or heterocyclic character. Also included are the bases or their salts.

Specific examples of cationic surfactants that we have found to be especially suitable for use in our invention are as follows:

Monosoyatrimethylammonium chloride
Monococotrimethylammonium chloride
Monocottonseed oil trimethylammonium chloride
Monostearyltrimethylammonium chloride
Monooleyltrimethylammonium chloride
Di(hydrogenated tallow)dimethylammonium chloride
Dilauryldimethylammonium chloride
Monopalmityltrimethylammonium chloride
Distearyldimethylammonium chloride
Dicocodimethylammonium chloride
Myristyldimethylbenzylammonium chloride
Disoyamethylbenzylammonium chloride
Dioleylmethylbenzylammonium chloride
Mono(hydrogenated tallow)trimethylammonium chloride
Methylbis(2-hydroxyethyl)cocoammonium chloride
Methylpolyoxyethylene(15)cocoammonium chloride
Alkyl($C_{12}$–$C_{18}$)dimethylbenzylammonium chloride
Alkyl($C_{12}$–$C_{18}$)trimethylammonium chloride
Hexadecylamine acetate
Octadecylamine acetate
Cocoamine acetate
Tallowamine acetate
Di(hydrogenated tallow)amine acetate As to the amount of the two components comprising our debonding composition, that may vary as follows: 10 to 90 weight percent of the cationic surfactant and 90 to 10 weight percent of the dimethylamide of the carboxylic acid. In general, we have found that excellent debonding results are attained when our debonding composition is used in an amount varying from about 0.1 to 2.0 parts per 100 parts of cellulose pulp fiber based on the dry weight of said fiber. It will be understood, of course, that larger quantities may be used, but such is generally not desirable because costs are increased without commensurate additional beneficial results.

In order to disclose the nature of the invention still more clearly, the following illustrative examples will be given. It is understood, however, that the invention is not to be limited to the specific conditions or details set forth in these examples, except insofar as such limitations are specified in the appended claims.

The additives of this invention were used in the treatment of wet bleached pine kraft pulp in the form of an aqueous slurry with a pulp consistency of 0.5 percent. Handsheets were formed from the pulp on a laboratory handsheet machine to produce 20 cm×20 cm pulp sheets with basis weights of 120 g/m². After the sheets were formed, pressed, and dried by the standard procedure, the debonding effect was evaluated by determining the fiber-to-fiber internal bonding strength of these sheets by means of a Scott Internal Bond Tester as described in TAPPI UM-403. The effect on the hydrophilicity of the pulp was evaluated by measuring the water absorbency of these sheets by the Klemm procedure as described in SCAN P-13:64. The debonding effect was expressed as a percentage factor calculated as follows:

$$\text{Internal Bond Factor} = \frac{(\text{Internal Bond of Treated Pulp Sheet}) \times 100}{\text{Internal Bond of Untreated Pulp Sheet}}$$

Thus, the untreated pulp would have an Internal Bond Factor of 100 and debonded pulp would have Internal Bond Factors below 100; the lower this factor, the greater the degree of debonding achieved. The effect of the additives on the water absorbency as measured by the Klemm test is expressed as the height (mm) the water reaches in a vertical strip of the pulp sheet at a fixed time (10 min) after the strip is dipped 10 mm into the water. From these Klemm test data, a percentage factor was calculated as follows for comparison purposes:

$$\text{Hydrophilicity Factor} = \frac{(\text{mm Water Absorbency of Treated Pulp Sheet}) \times 100}{\text{mm Water Absorbency of Untreated Pulp Sheet}}$$

Thus, the untreated pulp would have a Hydrophilicity Factor of 100. Hydrophilicity Factors below 100 would indicate loss of water absorbency; the lower this factor, the greater the loss of water absorbency.

EXAMPLE 1

Additive A was prepared by mixing 50 percent by weight of DMA with 50 percent by weight of an 80 percent by weight solution of n-alkyl(50% $C_{14}$, 40% $C_{12}$, 10% $C_{16}$) dimethylbenzylammonium chloride. Thus, Additive A contained 50 percent DMA and 40 percent cationic surfactant. For comparison purposes, the components of Additive A were tested separately as debonding additives.

Additive B was composed solely of DMA and Additive C was composed solely of the 80 percent solution of the n-alkyldimethylbenzylammonium chloride described above.

Table 1 shows the results obtained with these three additives when they were evaluated by the indicated test methods. Treatment rates are in weight percent based on the dry weight of the pulp.

TABLE I

| Additive | Treatment Rate (%) | Internal Bond Factor | Hydrophilicity Factor |
|---|---|---|---|
| none | — | 100 | 100 |
| A | 0.5 | 53 | 98 |

TABLE I-continued

| Additive | Treatment Rate (%) | Internal Bond Factor | Hydrophilicity Factor |
|---|---|---|---|
| B | 0.5 | 100 | 95 |
| C | 0.5 | 100 | 80 |

These results show that Additive A is a good debonding agent, reducing the internal bond strength of the treated pulp to 53 percent of that of the original untreated pulp. However, the components of Additive A, that is, Additives B and C, when used separately for the treatment of the pulp had no debonding effect. Thus, a true synergism is demonstrated between the two essential components of the additives of this invention.

EXAMPLE 2

Additive D was prepared by mixing 50 percent by weight of DMA with 50 percent by weight of a 75 percent active solution of di(hydrogenated tallow)-dimethylammonium chloride. The latter is a commercially available substance sold under the trademark Arquad 2HT75, falling under U.S. Pat. No. 3,395,708, and used as a debonding agent in the manufacture of cellulose fluff. Thus, Additive D contained 50 percent dimethylamides and 37.5 percent cationic surfactant. For comparison purposes, the Arquad 2HT75 was run separately in our tests and is designated as Additive E.

Table II shows the results obtained with these two additives. Additive B, described in Example 1, is the other component of Additive D, and the results obtained with it are repeated in Table II for comparison.

TABLE II

| Additive | Treatment Rate (%) | Internal Bond Factor | Hydrophilicity Factor |
|---|---|---|---|
| none | — | 100 | 100 |
| D | 0.5 | 42 | 80 |
| E | 0.5 | 49 | 54 |
| B | 0.5 | 100 | 95 |

These results demonstrate that combining a commercially used quaternary ammonium chloride debonding agent with DMA in accordance with the teachings of this invention, provides an improved debonding effect. Also, the water absorbency of the pulp treated with the combination is much better than that of the pulp treated with the commercially used product.

EXAMPLES 3 to 15

A number of additives were prepared in accordance with this invention with N,N-dimethylamides derived from various fatty acids and with the use of various cationic surfactants. The proportion of the N,N-dimethylamides to cationic surfactant was also varied. The results of the tests on all these additives are shown in Table III. The composition of the additives is described below.

| Additive F | 50% DMA |
| | 25% monostearyltrimethylammonium chloride |
| | 25% solvent |
| Additive G | 50% DMA |
| | 25% monosoyatrimethylammonium chloride |
| | 25% solvent |
| Additive H | 50% DMA |
| | 38% dicocodimethylammonium chloride |
| | 12% solvent |
| Additive I | 50% DMA |
| | 27% alkyl($C_{16}$)dimethylbenzylammonium chloride |
| | 23% solvent |
| Additive J | 33% DMA |
| | 54% n-alkyldimethylbenzylammonium chloride of Example 1 |
| | 13% solvent |
| Additive K | 20% DMA |
| | 64% n-alkyldimethylbenzylammonium chloride of Example 1 |
| | 16% solvent |
| Additive L | 67% DMA |
| | 27% n-alkyldimethylbenzylammonium chloride of Example 1 |
| | 6% solvent |
| Additive M | 80% DMA |
| | 16% n-alkyldimethylbenzylammonium chloride of Example 1 |
| | 4% solvent |
| Additive N | 50% N,N—dimethylamides of byproduct acids from the dimerization of tall oil fatty acids |
| | 40% n-alkyldimethylbenzylammonium chloride of Example 1 |
| | 10% solvent |
| Additive P | 50% N,N—dimethylamides of soybean oil fatty acids |
| | 40% n-alkyldimethylbenzylammonium chloride of Example 1 |
| | 10% solvent |
| Additive Q | 50% N,N—dimethylamides of oleic acid |
| | 40% n-alkyldimethylbenzylammonium chloride of Example 1 |
| | 10% solvent |
| Additive R | 50% DMA |
| | 50% bis(2-hydroxyethl)oleylamine acetate |
| Additive S | 50% DMA |
| | 50% cocoamine acetate |

TABLE III

| Example | Additive | Treatment Rate(%) | Internal Bond Factor | Hydrophilicity Factor |
|---|---|---|---|---|
| 3 | F | 0.5 | 39 | 93 |
| 4 | G | 0.5 | 43 | 95 |
| 5 | H | 0.5 | 34 | 107 |
| 6 | I | 0.5 | 43 | 105 |
| 7 | J | 0.5 | 50 | 98 |
| 8 | K | 0.5 | 57 | 95 |
| 9 | L | 0.5 | 53 | 95 |
| 10 | M | 0.5 | 61 | 95 |
| 11 | N | 0.5 | 55 | 88 |
| 12 | P | 0.5 | 49 | 88 |
| 13 | Q | 0.5 | 50 | 80 |
| 14 | R | 0.5 | 45 | 83 |
| 15 | S | 0.5 | 55 | 83 |

Examples 3 to 6 demonstrate that a variety of quaternary ammonium compounds are suitable cationic surfactants in this invention. Examples 5 and 6 also show that treatment with additives of this invention sometimes increases the hydrophilicity over that of the original pulp. Examples 7 to 10 demonstrate that the ratios of the two essential components can be varied widely and still produce a good debonding effect. Examples 11 to 13 demonstrate that N,N-dimethylamides of a variety of fatty acids are suitable for this invention. Examples 14 and 15 show that cationic surfactants other than quaternary ammonium compounds are also suitable for this invention.

While particular embodiments of the invention have been described, it will be understood, of course, that the invention is not limited thereto since many modifications may be made thereof. It is, therefore, contemplated to cover by the appended claims any such modifications as fall within the true spirit and scope of the invention.

The invention having thus been described, what is claimed and desired to be secured by Letters Patent is:

1. A process for treating cellulose pulp fiber to reduce inter-fiber bonding, thus imparting a low degree of mechanical strength to webs formed therefrom, while at the same time, preserving good hydrophilic properties of said fiber which comprises adding to the cellulose pulp fiber slurry prior to or during the formation of the slurry into a web, a mixture comprising 10 to 90 weight percent of a cationic surfactant and 90 to 10 weight percent of a dimethylamide of a straight chain carboxylic acid characterized in that said carboxylic acid contains from 12 to 18 carbon atoms in an amount varying from 0.1 to 2.0 parts per 100 parts of said cellulose pulp fiber based on the dry weight of said fiber.

2. The method of claim 1 wherein the straight chain carboxylic acid is lauric acid.

3. The method of claim 1 wherein the straight chain carboxylic acid is myristic acid.

4. The method of claim 1 wherein the straight chain carboxylic acid is palmitic acid.

5. The method of claim 1 wherein the straight chain carboxylic acid is linoleic acid.

6. The method 1f claim 1 wherein the straight chain carboxylic acid is linolenic acid.

7. The method of claim 1 wherein the straight chain carboxylic acid is oleic acid.

8. The method of claim 1 wherein the straight chain carboxylic acid is ricinoleic acid.

9. The method of claim 1 wherein the straight chain carboxylic acid is stearic acid.

10. The method of claim 1 wherein the straight chain carboxylic acid is a mixture of straight chain carboxylic acids containing 18 carbon atoms and at least one carbon to carbon double bond.

11. The method of claim 1 wherein the straight chain carboxylic acid is a mixture of acids derived from tall oil.

12. The method of claim 1 wherein the straight chain carboxylic acid is a mixture of acids derived from soybean oil.

13. The method of claim 1 wherein the straight chain carboxylic acid is the byproduct acid from the dimerization of tall oil fatty acids.

14. The method of claim 1 wherein the cationic surfactant is an alkyl ($C_{12}$–$C_{18}$)dimethylbenzylammonium chloride.

15. The method of claim 1 wherein the cationic surfactant is an alkyl ($C_{12}$–$C_{18}$)trimethylammonium chloride.

16. The method of claim 1 wherein the cationic surfactant is a dialkyl ($C_{12}$–$C_{18}$)dimethylammonium chloride.

17. The method of claim 1 wherein the cationic surfactant is a dialkyl ($C_{12}$–$C_{18}$)methylbenzylammonium chloride.

18. The method of claim 1 wherein the cationic surfactant is a primary alkylamine salt.

19. The method of claim 1 wherein the cationic surfactant is a secondary alkylamine salt.

20. The method of claim 1 wherein the straight chain carboxylic acid is a mixture of acids derived from tall oil and the cationic surfactant is hexadecyldimethylbenzylammonium chloride.

21. The method of claim 1 wherein the straight chain carboxylic acid is a mixture of acids derived from tall oil and the cationic surfactant is hexadecyltrimethylammonium chloride.

22. The method of claim 1 wherein the straight chain carboxylic acid is a mixture of acids derived from soybean oil and the cationic surfactant is hexadecyltrimethylammonium chloride.

23. The method of claim 1 wherein the straight chain carboxylic acid is a mixture of acids derived from soybean oil and the cationic surfactant is hexadecyldimethylbenzylammonium chloride.

* * * * *